(12) United States Patent
Arvai et al.

(10) Patent No.: US 7,414,126 B2
(45) Date of Patent: Aug. 19, 2008

(54) PROCESS FOR THE PREPARATION OF TOPIRAMATE

(75) Inventors: Geza Arvai, Budapest (HU); Sandor Garaczi, Budapest (HU); Attila Gergely Mate, Budapest (HU); Ferenc Lukacs, Kistarcsa (HU); Zsolt Viski, Budapest (HU); Geza Schneider, Budapest (HU)

(73) Assignees: Helm AG, Hamburg (DE); CF Pharma Gyogyszergyarto Kft., Budapest (HU)

( * ) Notice: Subject to any disclaimer, the term of this patent is extended or adjusted under 35 U.S.C. 154(b) by 637 days.

(21) Appl. No.: 11/117,408

(22) Filed: Apr. 29, 2005

(65) Prior Publication Data

US 2006/0040874 A1   Feb. 23, 2006

(30) Foreign Application Priority Data

Aug. 19, 2004  (EP) .................................. 04019684

(51) Int. Cl.
*C07H 13/00* (2006.01)
*C07D 493/14* (2006.01)
(52) U.S. Cl. ......................................... 536/53; 549/387
(58) Field of Classification Search ................ 536/17.5, 536/53; 549/387
See application file for complete search history.

(56) References Cited

FOREIGN PATENT DOCUMENTS

EP   0 138 441 A2   4/1985

OTHER PUBLICATIONS

European Search Report for EP 04.019684.2 issued Mar. 2, 2005.

*Primary Examiner*—Bernard Dentz
(74) *Attorney, Agent, or Firm*—Chalin A. Smith; Smith Patent Consulting LLC

(57) ABSTRACT

The present invention relates to a process for the preparation of topiramate, intermediates in this process and a process for the preparation of these intermediates.

18 Claims, No Drawings

PROCESS FOR THE PREPARATION OF TOPIRAMATE

This application claims priority to European Patent Application No. 04.019684.2 filed Aug. 19, 2004, the contents of which are incorporated by reference herein in their entirety.

The present invention relates to a process for the preparation of topiramate, intermediates in this process and a process for the preparation of these intermediates.

Topiramate (2,3:4,5-bis-O-(1-methylethylidene)-β-D-fructopyranose sulfamate) of the formula I:

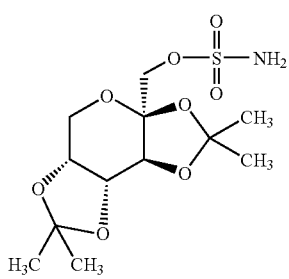

I is a known compound that has been found to exhibit anticonvulsant activity and thus is useful in the treatment of conditions such as epilepsy. This compound is disclosed in EP-A-0 138 441, which also discloses processes for the preparation of topiramate.

In EP-A-0 138 441 three reaction schemes are presented for the preparation of topiramate. Each process employs the readily available 2,3:4,5-bis-O-(1-methylethylidene)-β-D-fructopyranose of the formula II (see e.g. Brady et al. *Carbohydr. Res.* 15, 1970, 35-39),

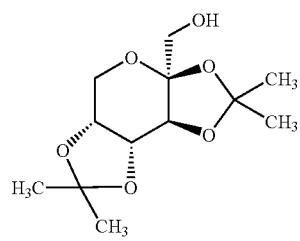

II as starting material and differs only in the way the sulfamate ester group is formed. The three processes comprise the following chemical steps.

In process A, the compound of formula II is reacted with sulfamoyl chloride of the formula $ClSO_2NH_2$ in the presence of sodium hydride using dimethylformamide (DMF) as solvent.

In process B, reacting the compound of formula II and sulfuryl chloride yields a chlorosulfate ester of formula V, which is then treated with a metal azide of the formula $MN_3$ and is finally reduced.

In process C, the chlorosulfate ester of formula V obtained according to process B is reacted with ammonia in methylene chloride or in acetonitrile.

The above processes A, B and C are summarized in the following reaction scheme 1:

Reaction scheme 1

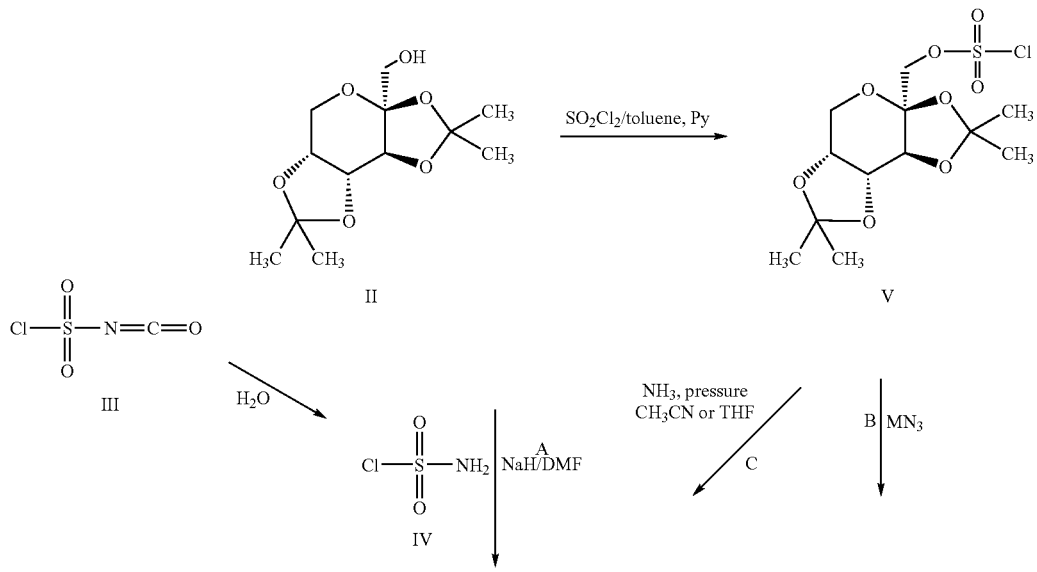

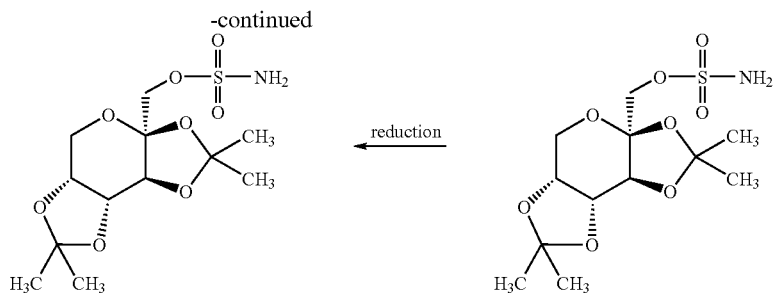

I

M = alkaline metal or ammonium

EP-A-0 533 483 describes the above process A as having two major disadvantages. One disadvantage is said to be that it calls for a combination of NaH and DMF which has an uncontrollable exotherm and is therefore potentially explosive. Another disadvantage is said to be that the process also used highly toxic and corrosive chlorosulfonyl isocyanate to prepare the commercially unavailable sulfamoyl chloride ($ClSO_2NH_2$). EP-A-0 533 483 discloses an improvement of process C, in which the reaction of the chlorosulfate ester of the formula V and pressurized ammonia is carried out in THF.

The above mentioned processes still suffer from the following disadvantages:

According to process A, sulfamoyl chloride of the formula $ClSO_2NH_2$ is employed, which is commercially unavailable. It is prepared by the partial hydrolysis of chlorosulfonyl isocyanate (*Chem. Ber.* 92, 1959, 509-513). Since chlorosulfonyl isocyanate reacts violently with water, the procedure can be conducted safely only in laboratory scale. Sulfamoyl chloride is extremely unstable and has to be used promptly after its preparation. Moreover, the highly flammable sodium hydride is utilized in the second step. Therefore this process is less suitable for industrial scale manufacturing.

According to process B, the chlorosulfate of the formula V is treated with the potentially explosive metal azide to obtain the azidosulfate of the formula VI. Azido compounds are dangerous to handle due to their explosive nature. Therefore they are not amenable to safe industrial application.

In process C, reaction of the chlorosulfate of the formula V and ammonia yields the sulfamate ester of formula I. According to EP-A-0 533 483 this process yields a product of low quality in mediocre yield. An improvement is presented in EP-A-0 533 483, which conducts the ammonolysis under pressure in THF to gain better yield and quality. Upon reproduction of the improved process the compound of formula I was obtained in 80-85% yield. However, even repeated recrystallisation sometimes failed to provide topiramate in pharmaceutical grade.

Thus, while the improved process C results in better yield of 80-85% and enhanced quality, nevertheless on reproducing the improved process, it was found that it is not possible to prepare in an acceptable quality and stable product even after repeated recrystallization. Topiramate thus obtained failed to pass the standard accelerated stability test, namely discoloration (decomposition) was observed.

Moreover, the preparation of the intermediate of the formula V by reacting the fructopyranose of the formula II with sulfuryl chloride is carried out in diluted solutions requiring a large amount of solvents. Furthermore, sulfuryl chloride has two reactive chloro groups so that the bis-addition product can be formed as undesired by-product. Finally, the Intermediate of formula V is obtained as an oil, which is difficult to purify and to store.

Also in the reaction of the intermediate of the formula V and ammonia bis-aducts and oligomers can be formed as undesirable by-products.

WO 03/097656 discloses N-substituted derivatives of topiramate and their use as intermediates in the preparation of topiramate. The N-substituted derivatives can be prepared by either reacting the compound of above formula V with an amine or by reacting an alcohol of above formula II with a chlorosulfonyl derivative of the formula $ClSO_2NHCOOR$, wherein R is alkyl, aryl or aralkyl.

When upscaling the process disclosed in WO 03/097656 it was found that the so prepared product was not always stable which raised doubts about the reproducibility of the process. Moreover, while according to WO 031097656 the sulfonyl carbamate intermediates can be converted into their salts (which would open up an easy purification method) the salt formation requires reaction with sodium hydride in a polar, aprotic solvent, such as THF.

There is still a need for an improved economical process for the preparation of topiramate. Therefore, an object of the present invention is to provide such process which provides topiramate not only in pharmaceutical grade but also in a highly stable form. Moreover, the process should be feasible in industrial scale. Preferably, the process should provide easy means for purification of the intermediates. Finally, the process should be safe and economical.

It has now surprisingly been found that the above problems can be solved by hydrolysing a compound of the general formula IX:

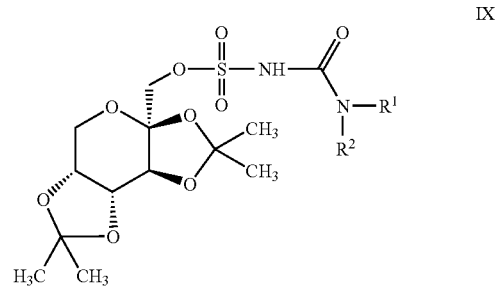

IX

Thus, the present invention relates to a process for the preparation of topiramate or a pharmaceutically acceptable salt thereof, which process comprises the step of hydrolysing a compound of the general formula IX:

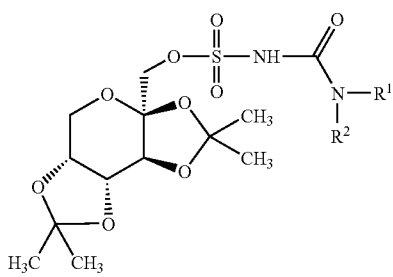

IX wherein $R^1$ and $R^2$ are independently selected from saturated or unsaturated, straight, branched and/or cyclic alkyl, aryl or aralkyl, or $R^1$ and $R^2$ taken together with the nitrogen atom to which they are bound form a saturated or unsaturated heterocyloalkyl.

Herein a saturated or unsaturated, straight, branched and/or cyclic alkyl group is preferably a straight or branched $C_{1-10}$, more preferably $C_{1-4}$ alkyl group, such as methyl, ethyl, n-propyl, isopropyl, n-butyl, isobutyl and tert-butyl. The cyclic alkyl group may be a $C_{3-5}$ cyclic alkyl group. These groups may be saturated or unsaturated, preferably saturated. The preferred alkyl is ethyl. Aryl may be for example phenyl or naphthyl, preferably phenyl. Aralkyl may be a combination of any of the aforementioned alkyl and aryl groups, preferably benzyl.

The saturated or unsaturated heterocycloalkyl formed when $R^1$ and $R^2$ are taken together with the nitrogen atom to which they are bound preferably has five or six ring atoms. Examples of such heterocycloalkyls include pyrrolidine, piperidine, piperazine and morpholine.

The hydrolysis of the compound of the general formula IX may for example be carried out in an aqueous solvent mixture, such as a mixture of water and a water-miscible organic solvent, such as acetone.

The pH of the reaction mixture is preferably adjusted in the range of 2-5, preferably 3.5-4.5 In a preferred embodiment of the process of the present invention the pH is maintained during hydrolysis of the compound of the general formula IX by using an appropriate buffer solution, such as a sodium acetate-acetic acid buffer solution.

The hydrolysis reaction may be conducted in a temperature range of for example 10-100° C., preferably 70-90° C.

The hydrolysis reaction may be carried out at any suitable pressure, such as atmospheric pressure or elevated pressure of for example between 1 and 5 bar, more preferably in the range of between 1 and 2 bar, to increase the temperature of the reaction mixture.

The intermediate compound of the general formula IX can be prepared by reacting 2,3:4,5-bis-O-(1-methylethylidene)-β-D-fructopyranose of the formula II

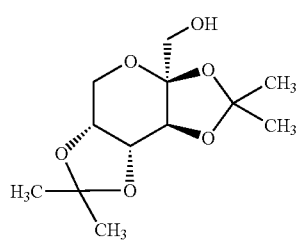

II with a substituted aminocarbonylsulfamoyl chloride of the general formula VIII

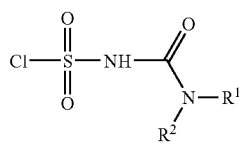

VIII wherein $R^1$ and $R^2$ are defined as above.

This reaction is preferably carried out in the presence of a base, preferably an organic amine base, most preferably an organic tertiary amine base, such as triethylamine. As solvent any suitable solvent may be employed, for example a chlorinated hydrocarbon, aromatic or ether-type solvent or acetonitrile, preferably methylene chloride, toluene or tetrahydrofurane (THF).

The reaction between the N-protected sulfamoyl chloride of the general formula VIII and the compound of the formula II can be carried out at a temperature of for example in the range of −30° C. to 80° C., preferably −15° C. to 0° C.

The molar ratio of the compounds of formula II and general formula VIII is not particularly relevant but preferably in the range of 1:1.5 to 1:0.5 (compound of formula II; compound of general formula VIII). More preferably this molar ratio is about equimolar, such as about 1:1.2.

The compound of the general formula VIII can be prepared by reacting chlorosulfonyl isocyanate (compound of formula III):

$$Cl-\underset{\underset{O}{\|}}{\overset{\overset{O}{\|}}{S}}-N-C=O$$

III with a compound of the general formula VII:

VII wherein $R^1$ and $R^2$ are defined as above.

The process of the present invention is summarized in the following reaction scheme 2:

Reaction Scheme 2

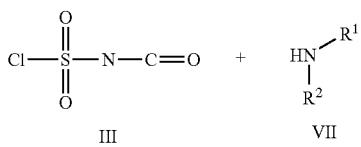

III    VII

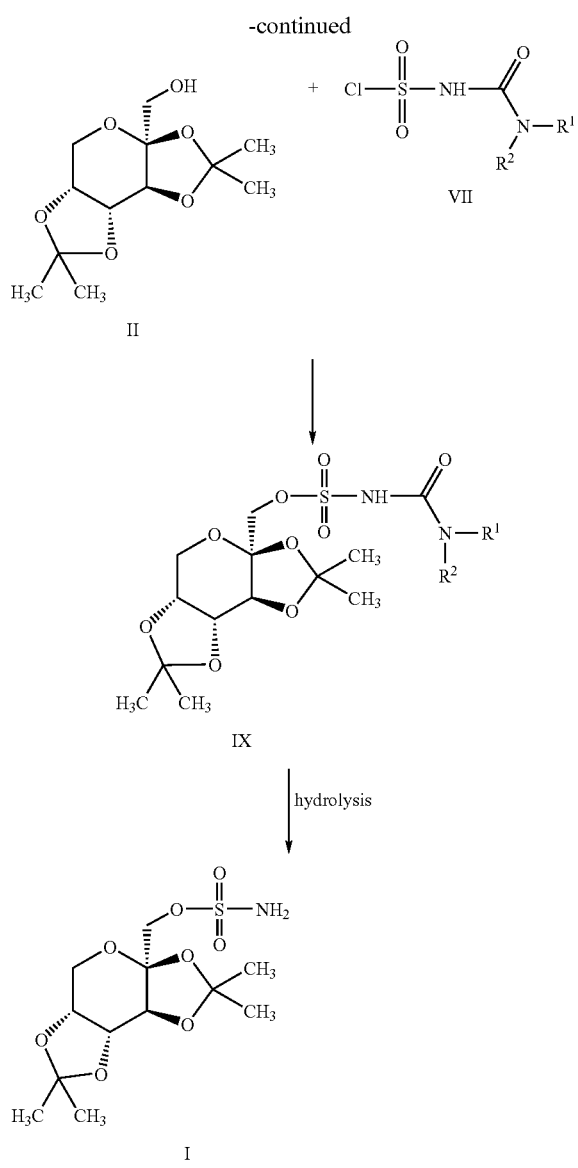

The process of the present invention can be carried out as one-pot reaction without isolating the intermediate compounds of the general formulae VIII and IX. The combined yield of the one-pot procedure is between 50 and 55%.

The present invention further relates to a compound of the above general formula IX or a salt thereof as well as to the use of this compound or a salt thereof for the preparation of topiramate or a pharmaceutically acceptable salt thereof.

Furthermore, the present invention relates to the use of a compound of the above general formula VII for the preparation of topiramate or a pharmaceutically acceptable salt thereof.

A particular advantage of the process of the present invention is that the N-acyl sulfaminic ester moiety in the compounds of the above general formula IX presents the opportunity of an easy purification method. The compounds of the general formula IX can readily be converted to a water-soluble salt on treatment for example with an aqueous base and most of the impurities, which do not contain a proper acidic functional group to form salts, can be removed by extraction with organic solvents. Examples of suitable bases include, but are not limited to, sodium hydroxide, potassium hydroxide, sodium carbonate and potassium carbonate. As organic solvents for extraction of the impurities ethers, such as diethylether and tert-butylmethylether, hydrocarbons, such as cyclohexane, aromatic hydrocarbons, such as toluene, or mixtures thereof can be used. The acidic form of the compound of general formula IX is then precipitated on treatment of the alkaline salt of this compound with a mineral or organic acid and recovered by filtration.

Therefore, preferred salts of the compound of the general formula IX are alkaline metal salts such as sodium and potassium salts.

The process of the present invention has the following advantages over the prior art processes:

Chlorosulfonyl isocyanate of formula III reacts violently with water. Consequently, no safe and industrial method is known in the prior art for manufacturing the resulting sulfamoyl chloride of formula $ClSO_2NH_2$. However, by replacing water with an appropriate secondary amine of the general formula VII and conducting the addition reaction in a suitable organic solvent, the N-protected sulfamoyl chloride of the general formula VIII can be prepared without difficulty even at industrial scale. The separation of the compounds of general formula VIII from the reaction medium is not necessary, they can be used directly and promptly after their preparation.

The N-protected sulfamoyl chloride of general formula VIII reacts with the monosaccharide of formula II in the presence of base such as triethylamine as opposed to the case of sulfamoyl chloride when sodium hydride in dimethylformamide is required to accomplish the reaction. No bis-adduct was formed in any of the reactions performed.

The synthesis of the sulfamoylating agent of general formula VIII as well as its subsequent reaction with the compound of formula II require only mild reaction conditions. Consequently the product of formula IX can be isolated in high yield and in pure form.

Due to the easy purification of the compound of general formula IX the topiramate prepared according to the present invention does not contain impurities detrimental to its stability. Topiramate obtained according the process of the present invention does not show discoloration (decomposition) during the accelerated storage test, which is standard procedure to characterise stability in pharmaceutical practice.

The protective $CONR_1(R_2)$ moiety in the compound of general formula IX is selectively removed in high yield by hydrolysis.

Topiramate prepared according to the present invention is suitable for producing pharmaceutical compositions due to its high purity and thermal stability.

The present invention is now illustrated by the following examples, which are not intended to limit the scope of the present invention.

EXAMPLES

Example 1

Preparation of N-[(dialkylamino)carbonyl], N-{[aryl (alkyl)amino]carbonyl} and N-[(diarylamino)carbonyl]-2,3:4,5-bis-O-(1-methylethylidene)-β-D-fructopyranose sulfamates (IX)

Example 1.1

N-[(Diphenylamino)carbonyl]-2,3:4,5-bis-O-(1-methylethylidene)-β-D-fructopyranose sulfamate (IX, $R_1$, $R_2$=phenyl)

Diphenylamine (9.72 g, 57.4 mmol) in methylene chloride (20 ml) is added dropwise to a solution of chlorosulfonyl isocyanate (8.94 g, 63.2 mmol) in methylene chloride (20 ml) under an atmosphere of dry argon while the temperature is kept at −20° C. After the addition is finished, the reaction mixture is stirred at −10° C. for 0.5 hours. The resulting solution of N,N-diphenyl-N'-chlorosulfonyl urea is cooled to −25° C., and a mixture of 2,3:4,5-bis-O-(1-methylethylidene)-β-D-fructopyranose (13.45 g, 51.7 mmol) and triethylamine (8.03 g, 79 mmol) in methylene chloride (20 ml) is added dropwise while the temperature of the reaction mixture is maintained between −20 and −15° C. It is then stirred at 5° C. and the progress of the reaction is monitored by TLC analysis. When completion is reached, the reaction mixture is washed with water (2×100 ml), dried on magnesium sulfate and concentrated at reduced pressure in a rotary evaporator. The resulting syrupy product weighs 28.0 g and is used in the next step without further purification.

Example 1.2

N-[(Diethylamino)carbonyl]-2,3:4,5-bis-O-(1-methylethylidene)-β-D-fructopyranose sulfamate (IX, $R_1$, $R_2$=ethyl)

1.2.1
A solution of chlorosulfonyl isocyanate (32 g, 0.226 mol) in methylene chloride (100 ml) is cooled to −25° C. under an atmosphere of dry argon. Diethylamine (16.52 g, 0.226 mol) in methylene chloride (100 ml) is then added dropwise while the temperature is kept at −20° C. After the addition is finished, the mature is warmed to 25° C. and stirred for 0.5 hours. It is then cooled to −25° C. and triethylamine (24.82 g, 0.245 mol) in methylene chloride (40 ml) is added followed by 2,3:4,5-bis-O-(1-methylethylidene)-β-D-fructopyranose (47 g, 0.18 mol) in methylene chloride (60 ml) while the temperature is maintained at −20° C. The resulting mixture is stirred at 25° C. and the progress of the reaction is monitored by TLC analysis. After 3 hours completion is reached. Most of the solvent is removed at reduced pressure in a rotary evaporator. The residue is dissolved in methanol (400 ml) and the solution is concentrated to about half its volume in a water bath of 40° C. at reduced pressure in a rotary evaporator. The solution is then cooled to 15° C. and upon slow addition of water (300 ml) white crystals precipitate. The product is collected by filtration, washed with cold water and dried overnight in vacuum at 40° C. Yield is 56.6 g (0.129 mol, 71.6%).

The crude product is recrystallised by dissolving in methanol (150 ml) at 40-45° C. and precipitating with water (225 ml) at 15° C. Yield is 42.7 g (0.097 mol, 54%).

Melting point (hot plate): 110-112° C.
$[\alpha]^{20}_D$=−43.7 (c=1.0, methanol)
Characteristic IR bands (cm$^{-1}$, KBr): 3447, 2989, 2945, 1654, 1477, 1378, 1193, 1159, 1102, 1071, 1058, 1018, 911, 831, 756.
$^1$H-NMR (methanol-$d_4$, 500 MHz) δ: 1.17 (t, J=7 Hz, 6H, N(CH$_2$CH$_3$)$_2$), 1.33, 1.42, 1.44, 1.52 (s each, 12 H overall, CH$_3$ isopropylidene), 3.27 and 3.39 (m each, 4H overall, N(CH$_2$CH$_3$)$_2$), 3.65 (d, 1H, J=13.0 Hz, H-6a). 3.93 (dd, 1H, J=13 and 1.5 Hz, H-6b), 4.18 (d, 1H, J=10 Hz, H-1a), 4.24 (d, 2H, J=10 Hz, H-1b and H-5), 4.49 (d, 1H, J=2.5 Hz, H-3), 4.62 (d, 1H, J=8 and 2.5 Hz, H-4).
$^{13}$C-NMR (methanol-$d_4$, 125 MHz) δ: 13.04, (N(CH$_2$CH$_3$)$_2$), 24.46, 25.88, 26.52, 26.91 (CH$_3$ isopropylidene), 42.91 (N(CH$_2$CH$_3$)$_2$), 62.60 (C-6), 71.33 (C-3), 71.54 (C-4), 71.65 (C-1), 72.33 (C-5), 102.20 (C-2), 110.31, 110.62 (Cq isopropylidene), 153.9 (C—O, missing in 1D spectrum, detectable in gs-HMBC 2D spectrum).

1.2.2
The crude product (25 g) obtained according to Example 1.2.1 is suspended in water (85 ml). 10 M sodium hydroxide (6.5 ml) is then added to obtain a clear solution at pH 12. Impurities are removed by extraction with t-butyl methyl ether (4×15 ml). The aqueous phase is treated with 85% phosphoric acid (3 ml) and followed by the addition of 1 M phosphoric acid (4 ml) to adjust the pH to 4. The precipitating white crystals are collected by filtration and dried in vacuum at 40° C. Yield is 18.6 g (74.4%).

1.2.3
A solution of chlorosulfonyl isocyanate (16 g. 0.113 mol) in acetonitrile (50 ml) is cooled to −25° C. under an atmosphere of dry argon. Diethylamine (8.26 g, 0.113 mol) in acetonitrile (50 ml) is then added dropwise while the temperature is kept at −20° C. After the addition is finished, the mixture is warmed to 10° C. and stirred for 0.5 hours. It is then cooled to −25° C. and triethylamine (12.41 g, 0.122 mol) in acetonitrile (20 ml) is added followed by 2,3:4,5-bis-O-(1-methylethylidene)-β-D-fructopyranose (20.8 g, 0.08 mol) in acetonitrile (55 ml) while the temperature is maintained at −20° C. The resulting mixture is let to warm to 15° C. and the progress of the reaction is monitored by TLC analysis. After 4 hours completion is reached. The reaction mixture is treated with water (50 ml) and extracted with toluene (4×80 ml). The collected organic phases are thoroughly extracted with 10% sodium carbonate (10×60 ml). The collected aqueous phases are extracted with tert-butyl methyl ether (3×80 ml) and then treated with 85% phosphorus acid (39 ml). White crystals precipitate between pH 3-4. The product is filtered, washed with cold water and dried in vacuum. Yield is 11.9 g (33.9%).

Example 1.3

N-{[methyl(phenyl)amino]carbonyl}-2,3:4,5-bis-O-(1-methylethylidene)-β-D-fructopyranose sulfamate (IX, $R_1$=methyl, $R_2$=phenyl)

A solution of chlorosulfonyl isocyanate (7 g, 50 mmol) in methylene chloride (20 ml) is cooled to −25° C. under an atmosphere of dry argon. Methylaniline (5.35 g, 50 mmol) in methylene chloride (20 ml) is then added dropwise while the temperature is kept at −20° C. After the addition is finished, the mixture is stirred at −20° C. for 20 min. To the resulting solution of N-methyl-N-phenyl-N'-chlorosulfonyl urea, a mixture of 2,3:4,5-bis-O-(1-methylethylidene)-β-D-fructopyranose (11.5 g, 44.3 mmol) and triethylamine (5.05 g, 50 mmol) in methylene chloride (20 ml) is added dropwise while the temperature of the reaction mixture is maintained between −20 and −15° C. When addition is completed, it is warmed to 20° C. and the progress of the reaction is monitored by TLC analysis. When completion is reached, the reaction mixtures is washed with water (3×30 ml), dried on magnesium sulfate and concentrated at reduced pressure in a rotary evaporator. The resulting syrupy product is dissolved in 1 M sodium-hydroxide (50 ml) and extracted with toluene (3×30 ml). Then the aqueous phase is acidified to pH 4 by 85% phosphoric acid and extracted with t-butyl methyl ether (3×30 ml). The collected organic layers are concentrated at reduced pressure in a rotary evaporator and the residue is treated with hexane to obtain the product as white crystals. Yield is 16.11 g (34 mmol, 77%).

Melting point (hot plate); 51-55° C.
$[\alpha]^{20}_D$=−44.2 (c=0.41, methanol)
Characteristic IR bands (cm$^{-1}$, KBr): 3397, 2992, 2938, 1706, 1598, 1456, 1384, 1208, 1189, 1071, 1009, 886.

¹H-NMR (CDCl₃, 500 MHz) δ: 1.35, 1.45, 1.48, 1.54 (s each, 12 H overall, CH₃ isopropylidene), 3.28 (s, 3H, NCH₃), 3.75 (d, 1H, J=13.0 Hz, H-6a), 3.90 (dd, 1H, J=13 and 1.5 Hz, H-6b), 4.24 (dd, 1H, J=7.5 and 1 Hz, H-5), 4.36 (d, 1H, J=10.5 Hz, H-1a), 4.41 (d, 1H, J=2.5 Hz, H-3), 4.49 (d, 1H, J=10.5 Hz, H-1b), 4.62 (d, 1H, J=8 and 2.5 Hz, H-4), 7.27 (m, 2H), 7.43 (m, 1 H), 7.49 (m, 2H).

¹³C-NMR (CDCl₃, 125 MHz) δ: 24.35, 25.33, 26.12, 26.69 (CH₃ isopropylidene), 37.89 (NCH₃), 61.60 (C-6), 70.23, 70.40, 70.86 (CH). 72.82 (C-1), 100.79 (C-2), 109.36, 109.59 (Cq isopropylidene), 127.31, 129.34, 130.97 (CH aromatic), 141.12 (C-1 aromatic), 149.93 (C—O).

Example 2

Preparation of Topiramate by Hydrolysis of N-[(dialkylamino)carbonyl], N-{[aryl(alkyl)amino]carbonyl} and N-[(diarylamino)carbonyl]-2,3:4,5-bis-O-(1-methylethylidene)-β-D-fructopyranose sulfamates

Example 2.1

The crude product obtained in Example 1.1 is dissolved in acetone (15 ml) and sodium acetate-acetic acid buffer solution (prepared by treating a solution of glacial acetic acid (13 ml) and water (15 ml) with 10 M sodium hydroxide (ca. 4 ml) to adjust the pH of the mixture to 3.5). The reaction mixture is heated to reflux at (68-70° C.) for 1-1.5 hours when TLC analysis shows the consumption of the starting material. The cooled mixture is diluted with water (15 ml) and made alkaline with 10 M sodium hydroxide (ca. 26 ml, pH-13-14). It is then extracted with t-butyl methyl ether (2×50 ml and 1×25 ml). The aqueous phase is treated with 85% phosphoric acid to adjust the pH to 5.5-6 and white crystals precipitate on cooling to 10° C. The product is collected by filtration, washed with cold water and dried overnight in vacuum at 40° C. Yield is 11.75 g (34.6 mmol, 67%).

The purity may be increased by recrystallisation from a mixture of 2-propanol (12 ml) and water (48 ml).

Melting point: 125-126° C.
[α]²⁰_D=-32 (c=0.4, methanol)
HPLC (area %): 99.8

Example 2.2

The N-(diethylamino)carbonyl derivative prepared according to Example 1.2 (5 g) is dissolved in a mixture of acetone (12 ml), acetic add (11 ml) and water (12.5 ml) and the pH is adjusted to 2.5 by 1 M sodium hydroxide (0.4 ml). The resulting solution is heated to reflux at 78-79° C. After 1 hour TLC shows the consumption of the starting material. The cooled mixture is neutralised with 10 M sodium hydroxide and extracted with methylene chloride (4×15 ml). The collected organic phases are dried on magnesium sulphate and concentrated to obtain the crude product as syrup (5.5 g). It is then crystallised from 2-propanol (4 ml) and water (14.5 ml) to give white crystals. Yield is 2.95 g.

HPLC (area %): 99.8

Further examples are presented in Table 1

TABLE 1

| Example | pH | Time hour | Yield % | HPLC area % |
|---------|-----|-----------|---------|-------------|
| 2.2.1 | 3.0 | 1.5 | 83.2 | 99.8 |
| 2.2.2 | 3.5 | 1 | 72 | 99.6 |
| 2.2.3 | 4.0 | 3 | 69 | 99.7 |
| 2.2.4 | 4.5 | 3 | 61 | 99.6 |
| 2.2.5 | 5.0 | 8.5 | 77 | 99.1 |

Example 2.3

A mixture of the N-[methyl(phenyl)amino]carbonyl derivative prepared according to Example 1.3 (30.7 g. 65 mmol), acetone (30 ml) and sodium acetate-acetic acid buffer (pH 3.5, 35 ml) is heated to reflux (70° C.) for 2-2.5 hours when TLC analysis shows the consumption of the starting material. The cooled mixture is made alkaline with 10 M sodium hydroxide (Ca. 45 ml, pH=13-14). It is then extracted with t-butyl methyl ether (2×50 ml and 1×25 ml). The aqueous phase is treated with 85% phosphoric acid to adjust the pH to 5.5-6. 2-Propanol (20 ml) is added and the mixture is cooled to 10° C. to precipitate the product as off-white crystals. The product is collected by filtration, washed with cold water and dried overnight in vacuum at 40° C. Yield is 13.9 g (41 mmol, 63%).

The crude product is recrystallized from a mixture of 2-propanol (14 ml) and water (50 ml).

Example 3

One-pot Procedure for the Preparation of Topiramate (I)

Example 3.1

A solution of chlorosulfonyl isocyanate (7.08 g, 0.05 mol) in acetonitrile (25 ml) is cooled to -25° C. under an atmosphere of dry argon. Diethylamine (3.66 g, 0.05 mol) in acetonitrile (25 ml) is then added dropwise while the temperature is kept at -20° C. After the addition is finished, the mixture is warmed to 10° C. and stirred for 0.5 hours. It is then cooled to -25° C. and triethylamine (6.07 g, 0.06 mol) in acetonitrile (10 ml) is added followed by 2,3:4,5-bis-O-(1-methylethylidene)-β-D-fructopyranose (10.41 g, 0.04 mol) in acetonitrile (25 ml) while the temperature is maintained at -20° C. The resulting mixture is let to warm to 15° C. and the progress of the reaction is monitored by TLC analysis. When completion is reached, sodium acetate-acetic acid buffer (30 ml, pH 3.5) is added and the mixture is heated to 80° C. and acetonitrile (70 ml) is slowly distilled. After 1.5-2 hours reaction is completed. The mixture is then cooled to room temperature and made alkaline by the addition of 5 M sodium hydroxide. The resulting solution is extracted with tert-butyl methyl ether (3×25 ml). The aqueous phase is neutralised with 85% phosphoric acid and extracted thoroughly with methylene chloride (5×20 ml). The collected organic phase is concentrated and the residue is dissolved in hot mixture of 2-propanol (7 ml) and water (25 ml) and crystallised at 0-5° C. Yield is 7.47 g (55%).

Example 3.2

A solution of chlorosulfonyl isocyanate (16.3 g, 0.12 mol) in methylene chloride (50 ml) is cooled to -25° C. under an atmosphere of dry argon. Diethylamine (8.49 g, 0.12 mol) in methylene chloride (50 ml) is then added dropwise while the temperature is kept at −20° C. After the addition is finished, the mixture is warmed to 30° C. and stirred for 0.5 hours. It is then cooled to −20° C. and triethylamine (12.41 g, 0.12 mol) in methylene chloride (10 ml) is added followed by 2,3:4,5-bis-O-(1-methylethylidene)-β-D-fructopyranose (23.1 g, 0.09 mol) in methylene chloride (30 ml) while the temperature is maintained at −15° C. The resulting mixture is stirred at 25° C. and the progress of the reaction is monitored by TLC analysis. When completion is reached (3.5-4 hours), sodium acetate-acetic acid buffer (50 ml, pH 3,5) and acetone (10 ml) are added and the mixture is heated to 50° C. After removal of methylene chloride by distillation, further buffer (10 ml) and acetone (10 ml) are added to the reaction mixture and it is refluxed at 76-77° C. After 1.5-2 hours reaction is completed. The mixture is then cooled to room temperature and made alkaline by the addition of 5 M sodium hydroxide. The resulting solution is extracted with tert-butyl methyl ether (3×25 ml). Volatiles are removed at reduced pressure and the product crystallises upon neutralisation with 85% phosphoric acid at 5-10° C. The crude product (17.0 g) is recrystallised from 2-propanol (15 ml) and water (50 ml). Yield is 15.3 g (50%).

The invention claimed is:

1. A process for the preparation of topiramate or a pharmaceutically acceptable salt thereof, which process comprises the step of hydrolysing a compound of the general formula IX:

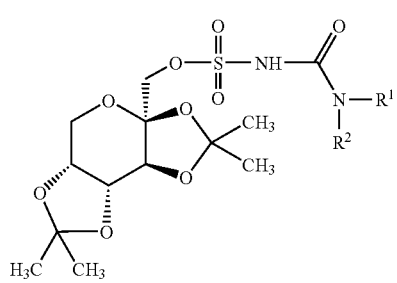

IX wherein $R^1$ and $R^2$ are independently selected from saturated or unsaturated, straight, branched and/or cyclic alkyl, aryl or aralkyl, or $R^1$ and $R^2$ taken together with the nitrogen atom to which they are bound form a saturated or unsaturated heterocycloalkyl.

2. A process for the preparation of a compound of the general formula IX:

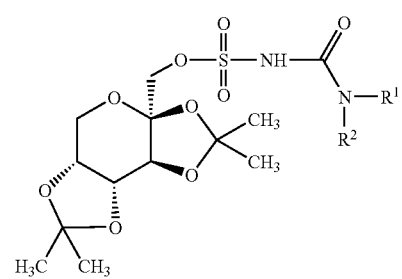

IX or a salt thereof, wherein $R^1$ and $R^2$ are independently selected from saturated or unsaturated, straight, branched and/or cyclic alkyl, aryl or aralkyl, or $R^1$ and $R^2$ taken together with the nitrogen atom to which they are bound form a saturated or unsaturated heterocycloalkyl, which process comprises the step of reacting a compound of the formula II:

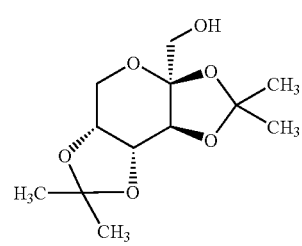

II with a compound of the general formula VIII:

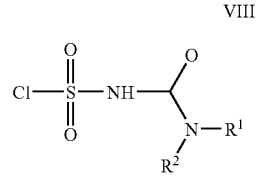

VIII wherein $R^1$ and $R^2$ are defined as above.

3. The process according to claim 2, wherein the reaction of the compounds of the formulae II and VIII is carried out in the presence of a base.

4. The process according to claim 1, wherein the compound of the general formula IX is obtained by a process that comprises the step of reacting a compound of the formula II:

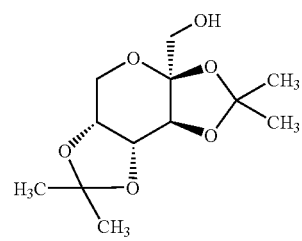

II with a compound of the general formula VIII:

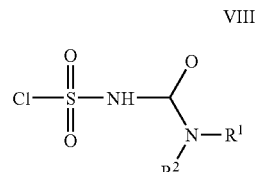

VIII wherein $R^1$ and $R^2$ are defined as above.

5. The process according to claim 2, wherein the compound of the general formula VIII is obtained by reacting chlorosulfonyl isocyanate with a compound of the general formula VII

VII wherein $R^1$ and $R^2$ are independently selected from saturated or unsaturated, straight, branched and/or cyclic alkyl, aryl or aralkyl, or $R^1$ $R^2$ taken together with the nitrogen atom to which they are bound form a saturated or unsaturated heterocycloalkyl.

6. The process according to claim 5, wherein the reaction is carried out as one-pot reaction without isolating the intermediate compounds of the general formulae VIII and IX.

7. The process according to claim 1, wherein $R^1$ and $R^2$ are ethyl.

8. A compound of the general formula IX:

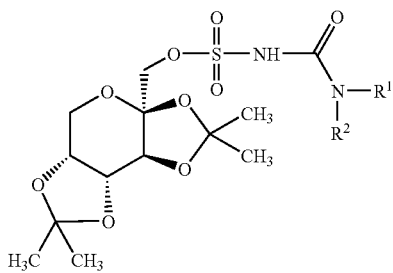

IX or a salt thereof, wherein $R^1$ and $R^2$ are independently selected from saturated or unsaturated, straight, branched and/or cyclic alkyl, aryl or aralkyl, or $R^1$ and $R^2$ taken together with the nitrogen atom to which they are bound form a saturated or unsaturated heterocycloalkyl.

9. A method of purifying a compound of the general formula IX:

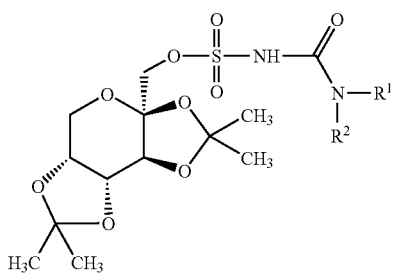

IX or a salt thereof, wherein $R^1$ and $R^2$ are independently selected from saturated or unsaturated, straight, branched and/or cyclic alkyl, aryl or aralkyl, or $R^1$ and $R^2$ taken together with the nitrogen atom to which they are bound form a saturated or unsaturated heterocycloalkyl, which method comprises preparing an aqueous solution of a water-soluble salt of the compound of the general formula IX and extracting said solution with an organic solvent.

10. The process according to claim 1, wherein the compound of the general formula IX is obtained by a process that comprises the step of reacting a compound of the formula II:

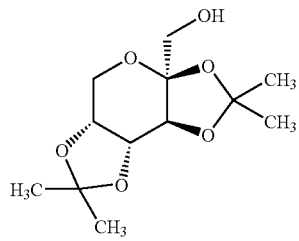

II with a compound of the general formula VIII:

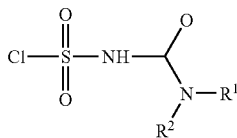

VIII wherein $R^1$ and $R^2$ are defined as above, further wherein the reaction of the compounds of the formulae II and VIII is carried out in the presence of triethylamine.

11. The process according to claim 3, wherein the compound of the general formula VIII is obtained by reacting chlorosulfonyl isocyanate with a compound of the general formula VII

VII wherein $R^1$ and $R^2$ are independently selected from saturated or unsaturated, straight, branched and/or cyclic alkyl, aryl or aralkyl, or $R^1$ and $R^2$ taken together with the nitrogen atom to which they are bound form a saturated or unsaturated heterocycloalkyl.

12. The process according to claim 11, wherein the reaction is carried out as one-pot reaction without isolating the intermediate compounds of the general formulae VIII and IX.

13. The process according to claim 4, wherein the compound of the general formula VIII is obtained by reacting chlorosulfonyl isocyanate with a compound of the general formula VII

VII wherein $R^1$ and $R^2$ are independently selected from saturated or unsaturated, straight, branched and/or cyclic alkyl, aryl or aralkyl, or $R^1$ and $R^2$ taken together with the nitrogen atom to which they are bound form a saturated or unsaturated heterocycloalkyl.

14. The process according to claim 13, wherein the reaction is carried out as one-pot reaction without isolating the intermediate compounds of the general formulae VIII and IX.

15. The process according to claim 2, wherein $R^1$ and $R^2$ are ethyl.

16. The process according to claim 3, wherein $R^1$ and $R^2$ are ethyl.

17. The process according to claim 4, wherein $R^1$ and $R^2$ are ethyl.

18. The process according to claim 5, wherein $R^1$ and $R^2$ are ethyl.

* * * * *